(12) United States Patent
Schenck et al.

(10) Patent No.: US 11,975,100 B2
(45) Date of Patent: May 7, 2024

(54) PROCESS FOR PREPARING PHARMACEUTICAL COMPOSITIONS

(71) Applicant: Merck Sharp & Dohme LLC, Rahway, NJ (US)

(72) Inventors: Luke R. Schenck, Yardley, PA (US); David J. Lamberto, Jackson, NJ (US); Joseph L. Kukura, II, Clark, NJ (US); Francisco J. Guzman, Jersey City, NJ (US); Aaron Cote, West Windsor, NJ (US); Athanas Koynov, Highland Park, NJ (US)

(73) Assignee: Merck Sharp & Dohme LLC, Rahway, NJ (US)

(*) Notice: Subject to any disclaimer, the term of this patent is extended or adjusted under 35 U.S.C. 154(b) by 0 days.

(21) Appl. No.: 17/489,296

(22) Filed: Sep. 29, 2021

(65) Prior Publication Data
US 2022/0016031 A1 Jan. 20, 2022

Related U.S. Application Data

(63) Continuation of application No. 16/061,513, filed as application No. PCT/US2016/066267 on Dec. 13, 2016, now abandoned.
(Continued)

(51) Int. Cl.
*A61K 9/14* (2006.01)
*A61K 9/51* (2006.01)

(52) U.S. Cl.
CPC ............ *A61K 9/145* (2013.01); *A61K 9/146* (2013.01); *A61K 9/5123* (2013.01);
(Continued)

(58) Field of Classification Search
CPC ...... A61K 9/145; A61K 9/146; A61K 9/5123; A61K 9/5138; A61K 9/5146; A61K 9/5161
See application file for complete search history.

(56) References Cited

U.S. PATENT DOCUMENTS

| | | | |
|---|---|---|---|
| 3,145,146 A | 8/1964 | Lieberman et al. | |
| 5,209,825 A * | 5/1993 | Badat | C07C 29/80 549/429 |

(Continued)

FOREIGN PATENT DOCUMENTS

| | | | |
|---|---|---|---|
| CN | 104434807 | * | 3/2015 |
| WO | 2011048491 | | 4/2011 |

OTHER PUBLICATIONS

Dodane et al., Pharmaceutical applications of chitosan, Pharmaceutical Science & Technology Today, Sep. 6, 1998, 246-253, 1-6.

*Primary Examiner* — Jianfeng Song
(74) *Attorney, Agent, or Firm* — Jeffrey P. Bergman; Catherine D. Fitch

(57) ABSTRACT

A process for preparing and isolating pharmaceutical active ingredient particles having a particle size of between about 0.1 and 30 microns, wherein a slurry comprising the active ingredient and one or more pharmaceutically acceptable excipients is fed into a thin film evaporator under suitable conditions for less than 10 minutes sufficient to generate solid matrix particles comprising active ingredient and one or more excipients, wherein the particles have less than 5% residual solvent.

15 Claims, 6 Drawing Sheets

Related U.S. Application Data

(60) Provisional application No. 62/423,518, filed on Nov. 17, 2016, provisional application No. 62/268,239, filed on Dec. 16, 2015.

(52) U.S. Cl.
CPC .......... *A61K 9/5138* (2013.01); *A61K 9/5146* (2013.01); *A61K 9/5161* (2013.01)

(56) References Cited

U.S. PATENT DOCUMENTS

| | | | |
|---|---|---|---|
| 8,663,658 B2* | 3/2014 | Park | A61K 9/1617 514/275 |
| 2003/0175338 A1 | 9/2003 | Singh et al. | |
| 2006/0106230 A1 | 5/2006 | Pinchasov et al. | |
| 2008/0207626 A1 | 8/2008 | Jungles et al. | |
| 2013/0171223 A1* | 7/2013 | Zhou | A61K 8/67 514/252.19 |
| 2015/0025080 A1* | 1/2015 | Kaushik | C07D 487/04 514/249 |

* cited by examiner

PROCESS FOR PREPARING PHARMACEUTICAL COMPOSITIONS

CROSS-REFERENCE TO RELATED APPLICATIONS

This application is a continuation of pending U.S. Ser. No. 16/061,513, filed Jun. 12, 2018, which is the National Stage application of PCT/US2016/066267, filed Dec. 13, 2016, which claims the benefit of U.S. Provisional Application Ser. No. 62/423,518, filed Nov. 17, 2016, and U.S. Provisional Application Ser. No. 62/268,239, filed Dec. 16, 2015, each of which is incorporated herein by reference in their entirety.

BACKGROUND OF THE INVENTION

Processing of nanocomposite microparticles incorporating drug nanoparticles requires a drying step. Bhakay et al. *Drug Dev Ind Pharm,* 2014; 40(11): 1509-1522 describe enhanced recovery and dissolution of griseofulvin nanoparticles from surfactant-free nanocomposite microparticles incorporating wet-milled swellable dispersants. Cerderia et al. *International Journal of Pharmaceutics* 443 (2013) 209-220 describe formulation and drying of miconazole and itraconazole nanosuspensions. Chen et al. *Drug Development and Industrial Pharmacy,* 35:283-296, 2009 describe flocculation of polymer stabilized nanocrystal suspensions to produce redispersible powders. Chin et al *Journal of Pharmaceutical Sciences* 103:2980-2999, 2014, describe processing of nanosuspensions to a final drug product. Hu et al. *Drug Development and Industrial Pharmacy* vol. 30, No. 3, pp. 233-245, 2004 describe nanoparticle engineering processes for enhancing the dissolution rates of poorly water soluble drugs. Kim et al. *International Journal of Pharmaceutics* 397 (2010) 218-224 describe effective polymeric dispersants for vacuum, convection and freeze drying of drug nanosuspensions. Liu et al. *Pharm Res* (2015) 32:628-639 describe interaction studies between indomethacin nanocrystals and PEO/PPO copolymer stabilizers. Ozeki et al. *Current Pharmaceutical Design,* 2013, 19, 6259-6269 describe functionally engineered nanosized particles in pharmaceutics, and improved oral delivery of poorly water-soluble drugs. Shaw et al. *J Pharm Innov* (2014) 9:227-237 describe glibenclamide nanocrystals for bioavailability enhancement: formulation design, process optimization, and pharmacodynamic evaluation. The described techniques for preparing drug nanoparticles do not employ thin film evaporation.

Additional techniques for preparing nanoparticles and poorly water soluble compounds are described in the following patents and patent publications U.S. Pat. Nos. 4,826,689, 5,118,528, 6,350,786, 8,835,376, US20030152500, US20030044433, US20050139144, US20090297565, US20100310659, US20120129898, WO1996038131, and WO2008006716. The described techniques do not employ a thin film evaporator.

SUMMARY OF THE INVENTION

A process for preparing and isolating pharmaceutical active ingredient particles having a particle size of between about 0.1 and 30 microns, wherein a a dried solids-containing slurry comprising the active ingredient and one or more pharmaceutically acceptable excipients is fed into a thin film evaporator under shear, temperature and pressure conditions to provide turbulent mixing for less than 10 minutes and sufficient to generate solid matrix particles comprising the active ingredient and the one or more excipients, wherein the particles have less than 5% residual solvent.

DETAILED DESCRIPTION OF THE INVENTION

Figure 1A:
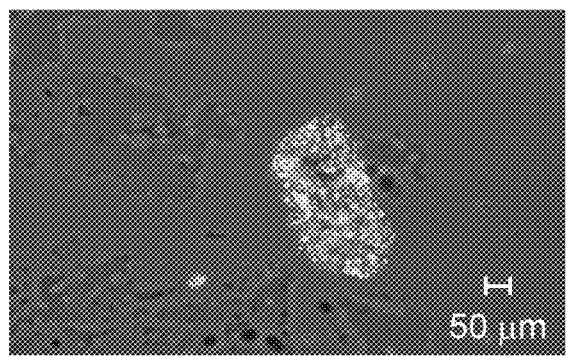
FIG. 1a is a monograph of the material of Example 1.

The invention is a process for preparing and isolating pharmaceutical active ingredient particles having a particle size of between about 0.1 and 30 microns, wherein a dried solids-containing slurry comprising the active ingredient and one or more pharmaceutically acceptable excipients is fed into a thin film evaporator under shear, temperature and pressure conditions to provide turbulent mixing for less than 10 minutes and sufficient to generate solid matrix particles comprising the active ingredient and the one or more excipients, wherein the particles have less than 5% residual solvent.

In one embodiment the invention is a process for preparing and isolating pharmaceutical active ingredient particles having a particle size of between about 0.1 and 30 microns, wherein a slurry comprising the active ingredient, a steric stability polymer, an electrostatic stability surfactant, and a redispersibility excipient, is fed into a thin film evaporator under shear, temperature and pressure conditions to provide turbulent mixing for less than 10 minutes and sufficient to generate solid matrix particles comprising the active ingredient and the one or more excipients, wherein the particles have less than 5% residual solvent.

In one embodiment the invention is a process for preparing and isolating pharmaceutical active ingredient particles having a particle size of between about 0.1 and 30 microns, wherein a slurry comprising the active ingredient and one or more pharmaceutically acceptable excipients is fed into a thin film evaporator under shear, temperature and pressure conditions to provide turbulent mixing for less than 5 minutes and sufficient to generate solid matrix particles comprising the active ingredient and the one or more excipients, wherein the particles have less than 0.5% residual solvent.

In an embodiment of the described process, the particles have a particle size of between 0.1 and 5 microns. In an embodiment of the described process, the particles have a particle size of between 0.1 and 0.25 microns. In an embodiment of the described processes, the particles are crystalline. In an embodiment of the described processes, the particles are amorphous.

In an embodiment of the described process, the slurry comprises active ingredient particles and an excipient which is a polymer that provides steric stability (a steric stability polymer). Examples of steric stability polymers that provide steric stability include but are not limited to cellulosic polymers (e.g., ethyl cellulose, methyl cellulose, hydroxyl propyl cellulose, hydroxylpropyl methyl cellulose, hydroxypropyl methyl cellulose acetate succinate, hydroxylpropyl methyl cellulose phthalate), methacrylates (e.g., Poly(butyl methacrylate-co-(2-dimethylaminoethyl), Poly(methacylic acid-co-ethyl acrylate), Poly(methacylic acid-co-methyl acrylate)), vinyl polymers (e.g., 1-ethenylpyrrolidin-2-one) copolymers (e.g., copovidone and soluplus(polyethylene glycol, polyvinyl acetate and polyvinylcaprolactame-based graft polymer, (PVAc-PVCap-PEG), BASF)), polyethylene glycol (e.g., polyethylene oxide (PEO) or polyoxyethylene (POE)), and/or poly(acrylic acid).

In an embodiment of the described process, the slurry comprises active ingredient particles and an excipient which is a surfactant that provides electrostatic stability (an electrostatic stability surfactant). Examples of electrostatic stability surfactants that provide electrostatic stability include but are not limited to Polyoxyethylene (20) sorbitan monooleate, poloxamer, Octadecanoic acid [2-[(2R,3S,4R)-3,4-dihydroxy-2-tetrahydrofuranyl]-2-hydroxyethyl] ester, Sodium 1,4-bis(2-ethylhexoxy)-1,4-dioxobutane-2-sulfonate, D-α-Tocopherol polyethylene glycol succinate, Sodium Lauryl Sulfate, and Lecithin.

In an embodiment of the described process, the slurry comprises active ingredient particles and an excipient that allows for redispersibility (a redispersibility excipient). Examples of redispersibility excipients that allow for redispersibility include but are not limited to salts, sugars, sugar alcohols, or polysacharrides. Among these excipients for redispersibility, preferred excipients are those that remain amorphous or partially amorphous following evaporative cooling including polymeric excipients also used for steric stabilization (see above, steric stability polymers), monosaccharides, disaccharides, amino acids and sugar alcohols. Excipients which are not in amorphous form which are isolated following thin film evaporation can optionally be added to improve processability, powder flow properties, and yield, and in the case of salt excipients, added to improve redispersibility.

Examples of salts include but are not limited to sodium chloride, potassium chloride, potassium carbonate, potassium sulfate, sodium bicarbonate, sodium phosphate, sodium sulfate, calcium phosphate and calcium carbonate. Among these, sodium carbonate and calcium phosphate are preferred.

Examples of monosaccharides include but are not limited to glucose, fructose, and galactose, and examples of disaccharides include but are not limited to lactose, maltose, sucrose, cellobiose, and trehalose. Among these examples, lactose and trehalose are preferred.

Examples of polysaccharides include but are not limited to raffinose, chitosan, and amylose.

Examples of sugar alcohols include but are not limited to mannitol, xylitol, sorbitol, and glycerol. Among these examples, mannitol is preferred.

In an embodiment of the described process, the suitable conditions to generate the solid matrix particles include vacuum, temperature between about 40° C. and 180° C., and shear sufficient to provide turbulent mixing. Preferred vacuum conditions are less that 100 mbar pressure. Appropriate mixing to keep an unstable turbulent boundary layer should involve Reynolds Numbers above 200,000 and shear rates exceeding 4,000 $s^{-1}$ In an embodiment of the described process, the particles are generated with top down milling operation involving wet processes such as media milling or high pressure homogenization. Wet processing may require physicochemical stabilization via steric and electrostatic routes with agents as described above. In an embodiment of the described process, the particles are generated with bottom up processing direct precipitation. Bottom up processing involves combination of active ingredient dissolved in a solvent that is combined with an anti-solvent in a turbulent field sufficient to achieve rapid mixing disperse precipitating particles. The extent of mixing required will be dependent on the nucleation kinetics of the active ingredient and can vary from milli-seconds to seconds. Mixing can be achieved with static mixers, mixing T's, high pressure homogenizer, rotor stator mills, or conventional overhead agitation with an impeller. Precipitation may be seeded to achieve desired crystalline form. In addition to mechanical optimization, the solvent or anti-solvent may include steric and/or electrostatic components for physicochemical stabilization.

In an embodiment of the process, the amount of active ingredient in the slurry dried solids is between about 20-80 wt/wt %. In another embodiment the amount of active ingredient in the slurry dried solids is between about 35-65 wt/wt %.

Thin Film Evaporation

Thin film evaporation is a technique for thermally separating materials in a mechanically generated, thin and highly turbulent liquid film. The technique is typically accomplished using a thin film evaporator.

A thin film evaporator consists of two major assemblies: a heated body and a rotor. The evaporator may be heated with any heat source including but not limited to steam, warm water, thermal oil or electricity. Elements of the evaporator system include an inner shell, a rotor blade system, and a gap between the rotor system and inner shell. As original wet fed product passes through the evaporator, a film zone, a bow wave, and a gap zone are formed by the product.

The original wet fed product requiring component separation enters above the evaporator heated zone and is evenly distributed by a rotating rotor over the evaporator's inner surface. The product spirals down the inner surface, developing rotor blade generated bow waves and highly turbulent flow, resulting in desirable heat flux and mass transfer. Volatile product components are rapidly evaporated. Vapors can be caused to flow either counter-currently or co-currently through the evaporator, depending on the application. In either case, vapors are subsequently condensed or further processed. Nonvolatile components are discharged at the evaporator outlet. The combination of 1) extremely short residence time, 2) narrow residence time distribution, 3) high turbulence, and 4) rapid surface renewal permits the thin film evaporator to successfully handle heat-sensitive, viscous and fouling-type fluids.

Thin film evaporators may be oriented horizontally or vertically. The working principles of horizontal and vertical thin film evaporators are similar.

A horizontal thin film evaporator may be cylindrical or conical in shape. A horizontal cylindrical evaporator includes a horizontal shell with heating jacket and a rotor in the shell which is equipped with rows of fixed blades. The fixed blades spread the original wet fed product requiring component separation in a thin layer over the heated wall. The thickness of the layer is defined by the clearance between the blade and the heated wall. A highly agitated bow wave is formed in front of the rotating blade. Turbulence increases as the product passes through the cylinder, and the volatile component evaporates continuously. The original wet fed product layer is a few millimeters in thickness. The blades of the rotor, which do not contact the evaporator inner surface, are designed to reduce fouling of the heat transfer surface by product. Pumps, screws or other feeding devices feed the product into the evaporator. The original wet fed product can be a thick liquid, a paste or a powder. The product is conveyed in a thin layer through the evaporator. Residence time is controlled by adjusting the blade configuration along the length of the rotor between mixing, conveying and cleaning blades. Produced vapor component which is removed from the original wet fed product passes counter-current to the product flow through the evaporator and in the direction of the vapor exit nozzle. Entrained fine particles are reagglomerated by contact with the original wet product feed. Produced free flowing powder component leaves the evaporator via a suitable air lock system. Alternatively, other produced components can result from the evaporator-treated product, including pastes, melts, and other forms containing an amount of volatile product component lower than that present in the original wet fed product. In one example of use of the horizontal cylindrical evaporator, the original wet fed product requiring component separation comes into contact with the rotor after entering the evaporator. The product is uniformly spread on the periphery by a distribution ring, then picked up by the first rotor blades and immediately formed in to a film (e.g., 0.5-3.5 mm in thickness) on the heat transfer surface. In front of each rotor blade, the fluid creates a bow wave. The fluid in the gap between the heat transfer surface and the rotor blade tip is highly turbulent, and this leads to intensive heat and mass transfer rates. This turbulence produces high heat transfer coefficients, even with highly viscous products. Due to the intensive mixing action within the bow wave, temperature sensitive products are prevented from overheating, and fouling on the heat transfer surface can be reduced or eliminated.

With a conical evaporator, original wet fed product requiring component separation is fed continuously to the conical evaporator at the larger diameter end, picked up by the rotor blades and spread immediately in a thin turbulent film on the heat transfer surface. The conical form results in a centrifugal force being imparted on the product by the rotor which effectively has two components: one perpendicular to the heat transfer surface and the other in the direction of the body's larger diameter end. The product hold up created by these forces and that of the incoming product ensures that the heat transfer surface is fully wetted independent of the evaporation ratio and/or the feed rate. Localized product overheating and thermal degradation are thereby reduced or avoided altogether. The product vapor flows co-currently through the evaporator and into the rotating separator. Here, entrained droplets and foam are knocked out and pass into the liquid phase outlet. The vapor then passes into the condensation stage, column or to another downstream stage.

Using a vertical thin film evaporator, original wet fed product requiring component separation is continuously fed into the above and is spread onto the periphery by the distribution ring. The fed product is then picked up by the rotor blades and immediately formed into a thin turbulent film on the heat transfer surface. The volatile components of the fed product are therefore very quickly evaporated and flow counter-currently with reference to the feed, up towards the top of the evaporator to the rotating separator. Here, entrained droplets or foam are knocked out of the vapor steam and return to the evaporation zone. The evaporated components then flow out of the evaporator to a condensation stage, column or to other downstream process step. Co-current vapor/product flow can also be used in which case a separation vessel is fitted at the bottom of the evaporator below the rotor in place of the normal rotor mounted separator and the upper vapor outlet nozzle. The non-volatile components of the fed product flow in a spiral path down the heat transfer surface to the bottom of the evaporator, arriving to the bottom part of the heat transfer zone in a single pass and leave the evaporator.

Micronized or nano sized materials offer increased in vivo exposure for poorly soluble compounds. A challenge with these fine materials is that while they can be processed and stabilized in a wet state as a suspension, drying these materials often results in irreversible aggregation such that the material no longer provides the benefits of micronized or nano sized materials. Dried material has appreciable benefits including the capacity for oral administration via conventional capsules or tablets. Additionally, dry products offer improved chemical stability, particularly for compounds sensitive to oxidation and hydrolysis. Additionally, the dry solids produced by the present process offer improved physical stability, where aggregation and particle growth via Ostwald ripening are reduced.

EXAMPLES

A common nanosuspension was prepared for the subsequent evaporative isolation experiments listed as examples 1 through 6. Here, the aqueous suspension/slurry involved 200 g/L of aprepitant, 50.125 g/L of HPC-LS as a steric stabilizer, and 0.9 g/L of sodium lauryl sulfate, an electrostatic stabilizer. The batch was milled using a Netzsch MiniCer. The milling chamber was filled with 300 micron yttrium stabilized spherical zirconia beads. Batch was pumped through the mill at 50 mL/min for a total of 9 batch turnovers with a rotor speed of 3900 rpm. This achieved the target terminal particle size, a nominal ×50 of 200 nm as measured via the Mastersizer 53000 static light scattering system.

A separate common nanosuspension was prepared for the subsequent evaporative isolation experiments listed as examples 7 and 8. Here an isopropyl alcohol based suspension/slurry involved 175 g/L of doravirine with 19.4 g/L polyvinylpyrrolidone as a steric stabilizer and 1.925 g/L of sorbitan monostearate added as an electrostatic stabilizer. The batch was milled using a Netzsch MiniCer. The milling chamber was filled with 300 micron yttrium stabilized spherical zirconia beads. Batch was pumped through the mill at 100 mL/min for a total of 20 batch turnovers with a rotor speed of 3600 rpm. This achieved the target terminal particle size, a nominal ×50 of 301 nm (meaning that 50% of the resulting material is smaller than 301 nm) as measured via the Mastersizer 53000 static light scattering system.

The thin film evaporator was based on a 0.5 square foot horizontal, counter current vapor/liquid flow configuration (Rototherm® (Artisan Industries, Inc. (Stoughton, MA)). Product contact parts are Hastelloy C276 and the distillate riser and condenser are 316 stainless steel) general shape (4 inch diameter rotor and auger. The auger is a ribbon blade design full helix with rotor at a $1/16^{th}$ of an inch clearance from the barrel walls), achievable temperature ranges (0-200° C.), achievable shear (variable frequency drive on the motor capable of running from 0-1800 rpm). Distillate riser includes a 2 inch opening, and a 2 inch product discharge outlet to facilitate powder flow.

Example 1

Figure 1B:
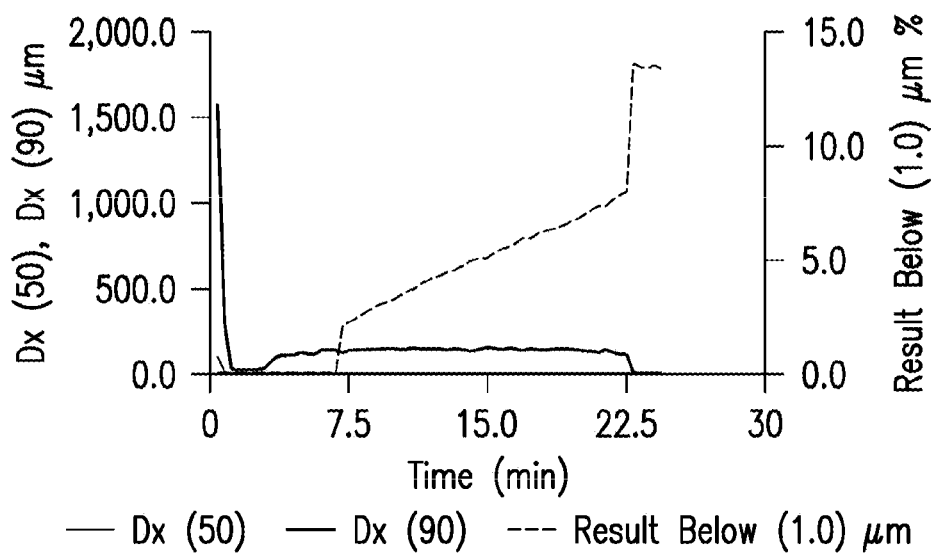
FIG. 1b shows particle size of material of Example 1 across a 30 min measurement window.
Figure 1C:
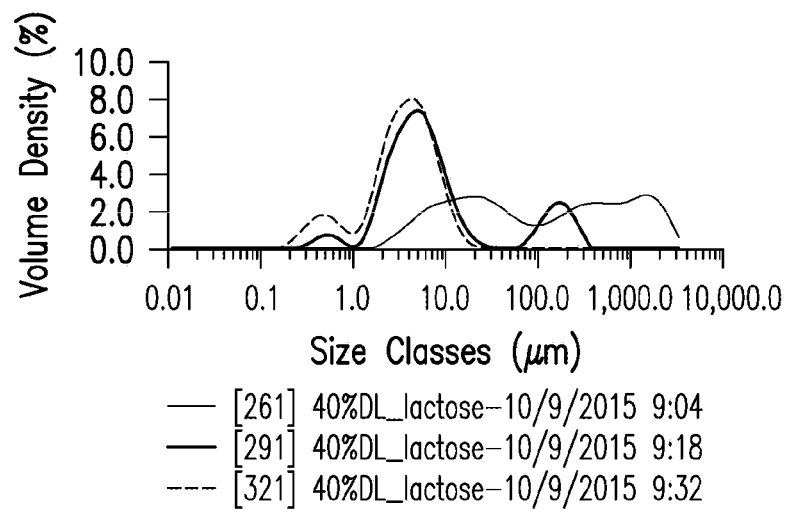
FIG. 1c shows the particle size distributions of materials of Example 1 at the beginning, mid-point at 15 minutes, and the end after sonication.

To the above slurry, 249 g/L lactose was added, so the final drug load of the active ingredient in the dried solids was 40 w/w %. This slurry was fed to the thin film evaporator (TFE) at 11 mL/min, dried at pressure of 30 mbar and temperature of 60° C. Isolated solids were evaluated with a kinetic redispersibility test, measuring particle size metrics as a function of time to determine if material would re-disperse to the target 200 nm. The kinetic redispersibility test involved measuring particle size across a 30 min period. Roughly 50 mg of sample was added to distilled water and stirred in the measurement cell at 2350 RPM. After 25 minutes, the sample was sonicated for 15 seconds at 65% power, followed by the collection of 5 additional measurements. FIG. 1a is a monograph of the resulting material. FIG. 1b shows the ×50 ( ——— ) ×90 ( ▬▬▬ ) and the percentage of particles <1 um across the 30 min measurement window ( ----- ). FIG. 1c shows the particle size distributions at the beginning ( ——— ), mid-point at 15 minutes ( ▬▬▬ ) and the end after sonication ( ------ ). The results highlight that only about 15% of resulting particles were less than 1 um, and the final ×50 is much higher than the target at approximately 3.6 microns.

Example 2

Figure 2A:
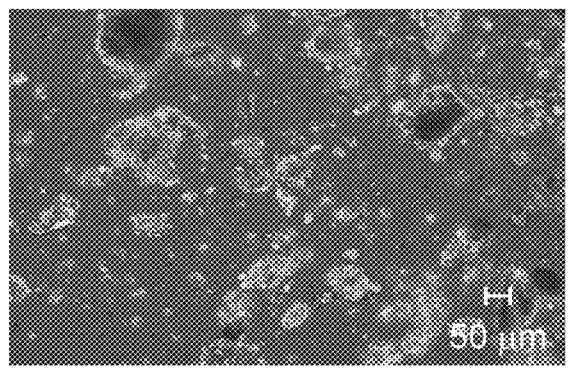
FIG. 2a is a monograph of the material of Example 2.
Figure 2B:
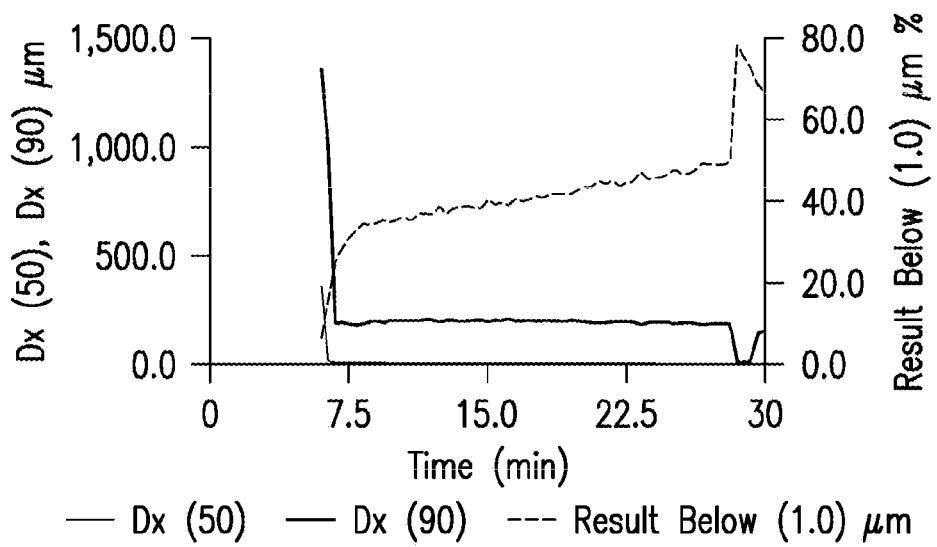
FIG. 2b shows particle size of material of Example 2 across a 30 min measurement window.
Figure 2C:
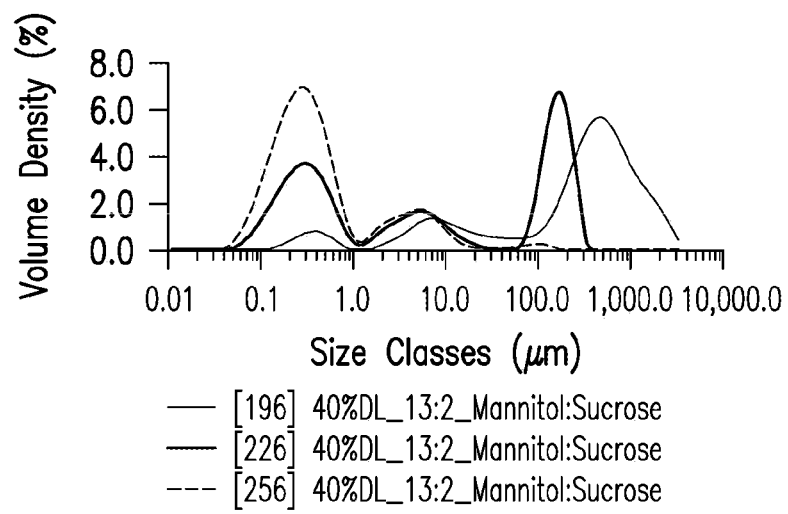
FIG. 2c shows the particle size distributions of materials of Example 2 at the beginning, mid-point at 15 minutes, and the end after sonication.

To the above slurry, 224 g/L mannitol and 25 g of sucrose were added, so the final drug load of the active ingredient in the dried solids was 40 w/w %. This slurry was fed to the TFE at 11 mL/min, dried at a pressure of 30 mbar and at a temperature of 60° C. Isolated solids were evaluated with a kinetic redispersibility test as outlined in Example 1, measuring particle size metrics as a function of time to determine if material would re-disperse to the target 200 nm. FIG. 2a is a micrograph of the material, and FIG. 2b and FIG. 2c show the particle size data. FIG. 2b shows the ×50 ( ——— ) ×90 ( ▬▬▬ ) and the percentage of particles <1 um across the 30 min measurement window ( ----- ). FIG. 2c shows the particle size distributions at the beginning ( ——— ), mid-point at 15 minutes ( ▬▬▬ ) and the end after sonication ( ----- ). This formulation achieved 80% of the particles in the sub-micron range, and the final ×50 near the target at 323 nm.

Example 3

Figure 3A:
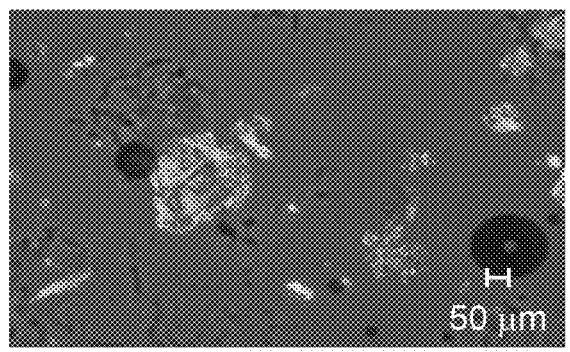
FIG. 3a is a monograph of the material of Example 3.
Figure 3B:
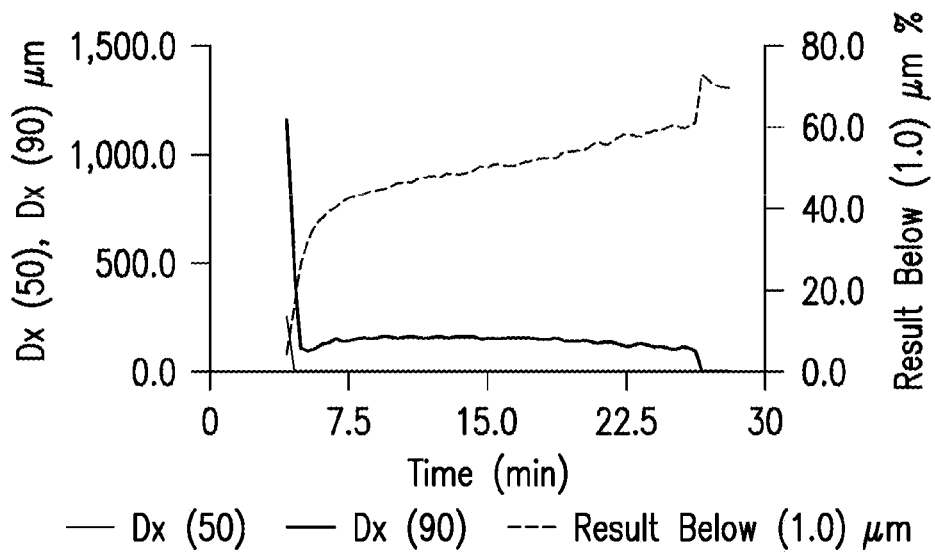
FIG. 3b shows particle size of material of Example 3 across a 30 min measurement window.
Figure 3C:
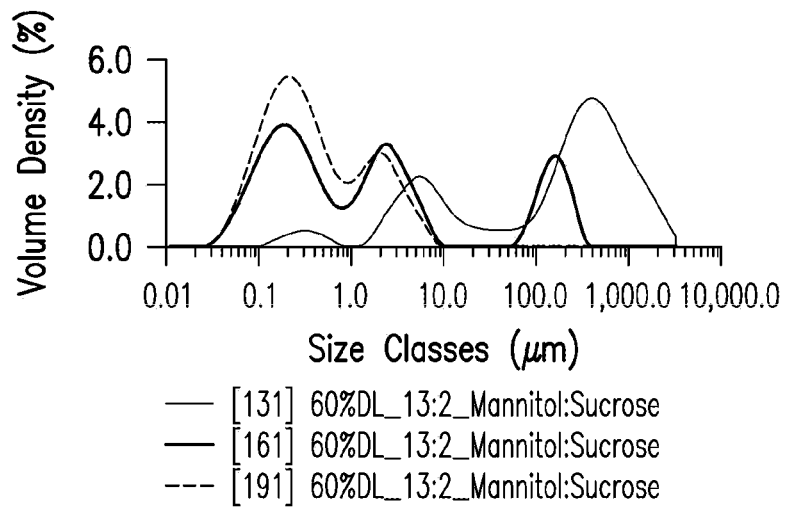
FIG. 3c shows the particle size distributions of materials of Example 3 at the beginning, mid-point at 15 minutes, and the end after sonication.

To the above slurry, 71 g/L mannitol and 11 g of sucrose were added, so the final drug load of the active ingredient in the dried solids was 60 w/w %. This slurry was fed to the TFE at 11 mL/min, dried at pressure of 30 mbar and a temperature of 60° C. Isolated solids were evaluated with a kinetic redispersibility test as outlined previously, measuring particle size metrics as a function of time to determine if material would re-disperse to the target 200 nm. FIG. 3a is a micrograph of the material, and FIG. 3b and FIG. 3c illustrate the particle size data (FIG. 3b and FIG. 3c). FIG. 3b shows the ×50 ( ——— ) ×90 ( ▬▬▬ ) and the percentage of particles <1 um across the 30 min measurement window ( ------ ). FIG. 3c shows the particle size distributions at the beginning ( ——— ), mid-point at 15 minutes ( ▬▬▬ ) and the end after sonication ( ------ ). This formulation achieved 75% of the particles in the sub-micron range, and the final ×50 near the target at 323 nm.

Example 4

Figure 4A:
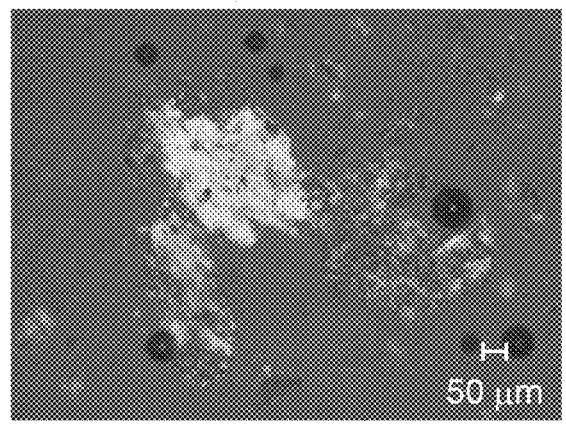
FIG. 4a is a monograph of the material of Example 4.
Figure 4B:
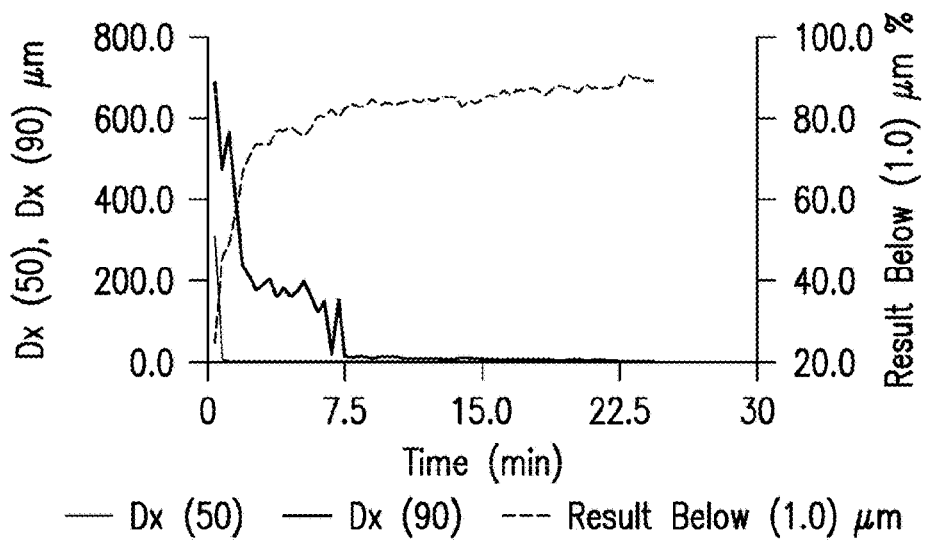
FIG. 4b shows particle size of material of Example 4 across a 30 min measurement window.
Figure 4C:
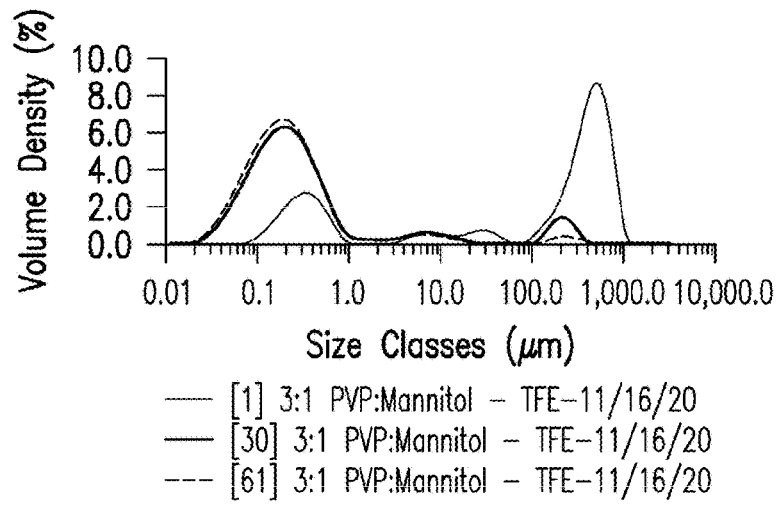
FIG. 4c shows the particle size distributions of materials of Example 4 at the beginning, mid-point at 15 minutes, and the end after sonication.

To the above slurry, 62 g of PVP and 20 g of mannitol were added, so the final drug load of the active ingredient in the dried solids was 60 w/w %. This slurry was fed to the TFE at 11 mL/min, dried at a pressure of 30 mbar and at a temperature of 60° C. Isolated solids were evaluated with a kinetic redispersibility test as outlined previously, measuring particle size metrics as a function of time to determine if material would re-disperse to the target 200 nm. FIG. 4a is a micrograph of the material, and FIG. 4b and FIG. 4c show the particle size data. FIG. 4b shows the ×50 ( ——— ) ×90 ( ▬▬▬ ) and the percentage of particles <1 um across the 30 min measurement window ( ----- ). FIG. 4c shows the particle size distributions at the beginning ( ——— ), mid-point at 15 minutes ( ▬▬▬ ) and the end after sonication ( ----- ). This formulation achieved 91% of the particles in the sub-micron range, and the final ×50 near the target at 209 nm.

Example 5

Figure 5A:
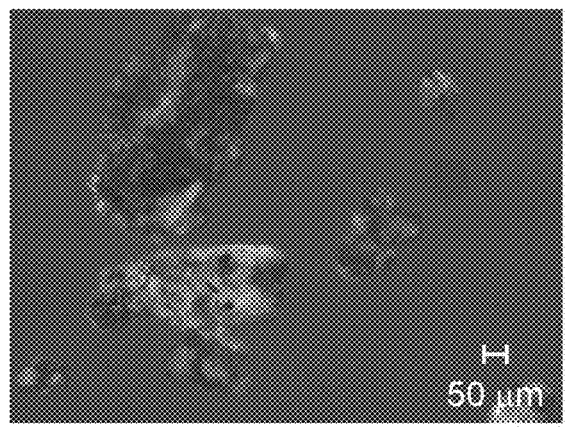
FIG. 5a is a monograph of the material of Example 5.
Figure 5B:
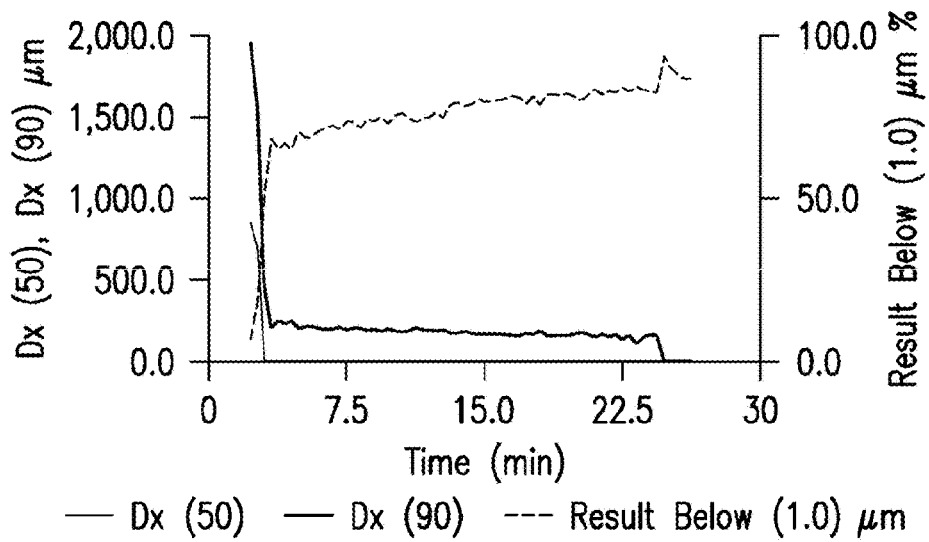
FIG. 5b shows particle size of material of Example 5 across a 30 min measurement window.
Figure 5C:
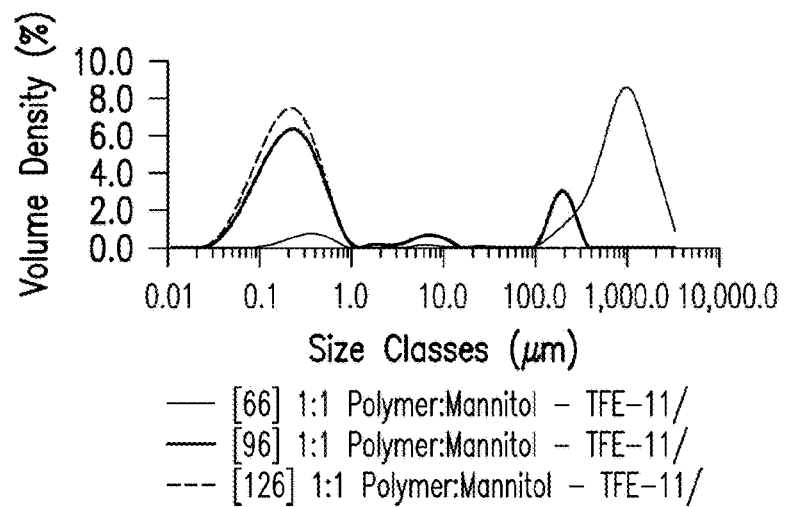
FIG. 5c shows the particle size distributions of materials of Example 5 at the beginning, mid-point at 15 minutes, and the end after sonication.

To the slurry above 62 g of PVP and 108 g of mannitol were added, so the final drug load of the active ingredient in the dried solids was 53 w/w %. This slurry was fed to the TFE at 11 mL/min, dried at a pressure of 30 mbar and at a temperature of 60° C. Isolated solids were evaluated with a kinetic redispersibility test as outlined previously, measuring particle size metrics as a function of time to determine if material would re-disperse to the target 200 nm. FIG. 5a is a micrograph of the material, and the particle size data is displayed in FIG. 5b and FIG. 5c). FIG. 5b shows the ×50 ( ——— ) ×90 ( ▬▬▬ ) and the percentage of particles <1 um across the 30 min measurement window ( ----- ). FIG. 5c shows the particle size distributions at the beginning ( ——— ), mid-point at 15 minutes ( ▬▬▬ ) and the end after sonication ( ----- ). This formulation achieved 95% of the particles in the sub-micron range, and the final ×50 near the target at 198 nm.

Example 6

Figure 6A:
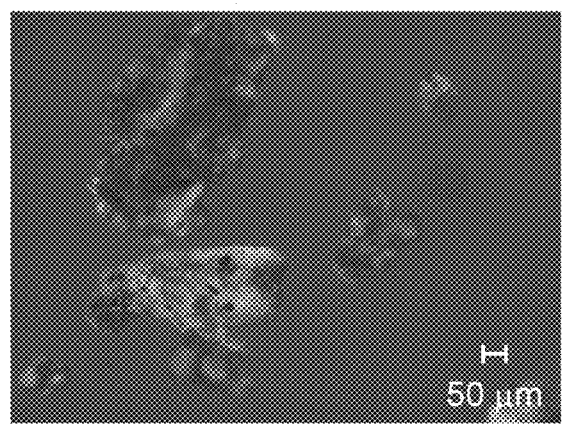
FIG. 6a is a monograph of the material of Example 6.
Figure 6B:
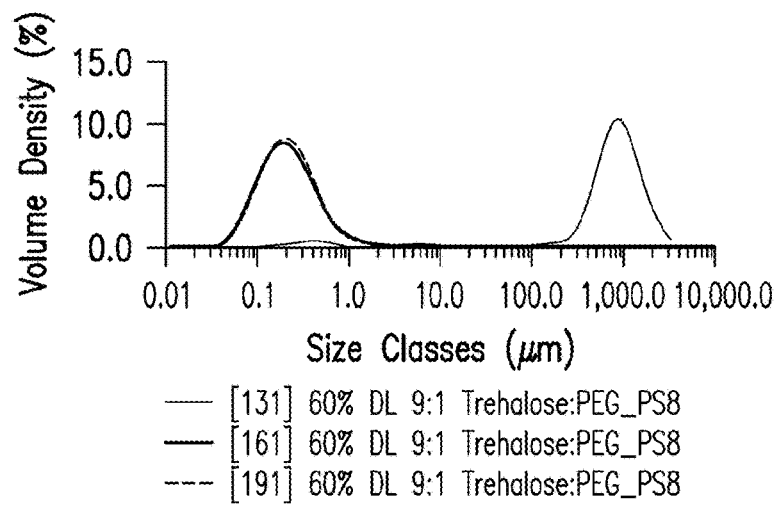
FIG. 6b shows particle size of material of Example 6 across a 30 min measurement window.
Figure 6C:
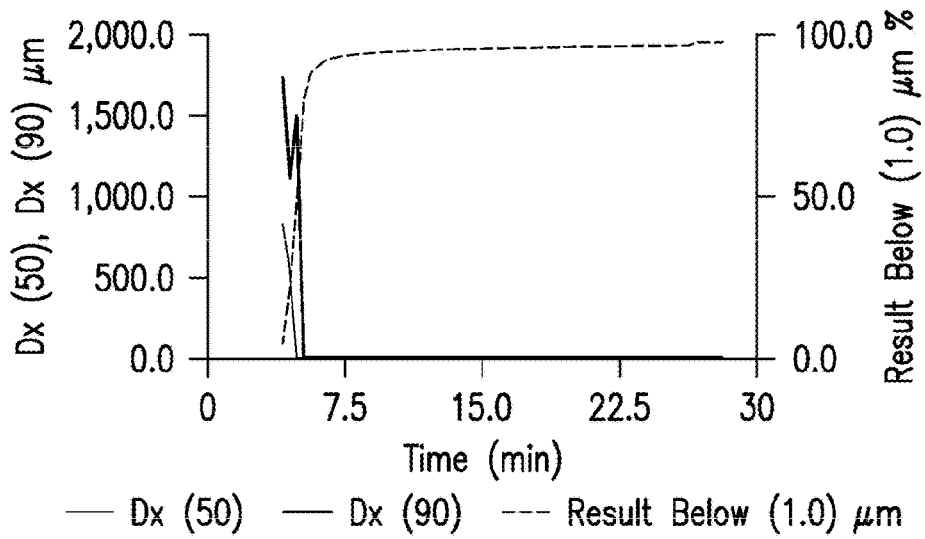
FIG. 6c shows the particle size distributions of materials of Example 6 at the beginning, mid-point at 15 minutes, and the end after sonication.

To the above slurry, 74 g/L of trehalose, and 8 g/L of polyethylene glycol 3350 and 1 g/L of Polysorbate 80 was added, so the final drug load of the active ingredient in the dried solids was 60 w/w %. This slurry was fed to the TFE at 11 mL/min, dried at a pressure of 30 mbar and at a temperature of 60° C. Isolated solids were evaluated with a kinetic redispersibility test as outlined previously, measuring particle size metrics as a function of time to determine if material would re-disperse to the target 200 nm. FIG. 6a is a micrograph of the material ( ), and the particle size data is shown in FIG. 6b and FIG. 6c. FIG. 6b shows the ×50 (———) ×90 (———) and the percentage of particles <1 um across the 30 min measurement window (-----). FIG. 6c shows the particle size distributions at the beginning (———), mid-point at 15 minutes (———) and the end after sonication (------). This formulation achieved 100% of the particles in the sub-micron range, and the final ×50 near the target at 195 nm.

Example 7

To a doravirine slurry prepared according to the procedure described above, 111.8 g/L of polyvinylpyrrolidone, and 43.8 g/L of mannitol were added, so the final drug load of the active ingredient in the dried solids was 50 w/w %. This slurry was fed to the TFE at 50 mL/min, dried at a pressure of 15 mbar and at a temperature of 65° C. Isolated solids were evaluated with a kinetic redispersibility test as outlined previously, measuring particle size metrics as a function of time to determine if material would re-disperse to the target 301 nm.

Redispersibility measurements as outlined above showed % particle size at the beginning as follows:
Particle Size Results—Beginning
10% of the particles are below 0.722 um
50% of the particles are below 9.25 um
90% of the particles are below 35.3 um
with 12% of the particle below 1 micron.

Redispersibility at the 15 minute middle time point showed % particle size achieved as follows:
Particle Size Results—15 Minute Middle Time Point
10% of the particles are below
0.380 um 50% of the particles are
below 5.18 um 90% of the
particles are below 19.4 um
with 25% of the particles below 1 micron.

Redispersibility at the end time point showed % particle size achieved as follows: Particle size results—15 minute middle time point
10% of the particles are below
0.143 um 50% of the particles
are below 0.304 um 90% of the
particles are below 0.672 um
with 95% of the particles below 1 micron.

Example 8

To the above doravirine slurry, 51.8 g/L of Poly(butyl methacrylate-co-(2-dimethylaminoethyl), and 103.8 g/L of mannitol was added, so the final drug load of the active ingredient in the dried solids was 50 w/w %. This slurry was fed to the TFE at 50 mL/min, dried at a pressure of 15 mbar and at a temperature of 45° C. Isolated solids were evaluated with a kinetic redispersibility test as outlined previously, measuring particle size metrics as a function of time to determine if material would re-disperse to the target 301 nm.

Redispersibility measurements as outlined above showed % particle size at the beginning as follows:
Particle Size Results—Beginning
10% of the particles are below
0.403 um 50% of the particles are
below 6.93 um 90% of the
particles are below 95.1 um
with 18% of the particle below 1 micron.

Redispersibility at the 15 minute middle time point showed % particle size achieved as follows:
Particle size results—15 minute middle time point 10% of
the particles are below 0.258 um
50% of the particles are below
3.81 um 90% of the particles
are below 78.3 um
with 39% of the particles below 1 micron.

Redispersibility at the end time point showed % particle size achieved as follows: Particle size results—15 minute middle time point
10% of the particles are below 0.105 um
50% of the particles are below 0.257 um
90% of the particles are below 0.690 um
with 92% of the particles below 1 micron.

What is claimed is:

1. A process for preparing and isolating pharmaceutical active ingredient particles having a particle size of between about 0.1 and 30 microns, wherein a dried solids-containing slurry comprising: (a) a pharmaceutical active ingredient, and one or more of: (b) a steric stability polymer, (c) an electrostatic stability surfactant, and (d) a redispersibility excipient, is fed into a thin film evaporator comprising shear rates exceeding 4,000 s$^{-1}$, temperature between about 50° C. and 100° C., vacuum from 10 mbar to 75 mbar pressure, and Reynolds Numbers above 200,000, to provide turbulent mixing for less than 10 minutes and sufficient to generate solid matrix particles comprising the pharmaceutical active ingredient and the one or more excipients, wherein the particles have less than 5% residual solvent.

2. The process of claim 1, wherein the dried solids containing slurry is fed into the thin film evaporator under shear, temperature and pressure conditions to provide turbulent mixing for less than 5 minutes.

3. The process of claim 2 wherein the particles have a particle size of between 0.1 and 5 microns.

4. The process of claim 1 wherein the particles are crystalline.

5. The process of claim 1 wherein the particles are amorphous.

6. The process of claim 1, wherein the steric stability polymer is a cellulosic polymer, a methacrylate, a vinyl polymer, a copolymer, or polyethylene glycol.

7. The process of claim 5 wherein the steric stability polymer is ethyl cellulose, methyl cellulose, hydroxyl propyl cellulose, hydroxylpropyl methyl cellulose, hydroxypropyl methyl cellulose acetate succinate, hydroxylpropyl methyl cellulose phthalate), poly(butyl methacrylate-co-(2-dimethylaminoethyl), poly(methacylic acid-co-ethyl acrylate), poly (methacylic acid-co-methyl acrylate), 1-ethenylpyrrolidin-2-one, copovidone, soluplus, polyethylene oxide (PEO), polyoxyethylene (POE), or poly(acrylic acid).

8. The process of claim 1 wherein the electrostatic stability surfactant is Polyoxyethylene (20) sorbitan monooleate, poloxamer, octadecanoic acid [2-[(2R,3S,4R)-3,4-dihydroxy-2-tetrahydrofuranyl]-2-hydroxyethyl] ester, sodium 1,4-bis(2-ethylhexoxy)-1,4-dioxobutane-2-sulfonate, D-α-Tocopherol polyethylene glycol succinate, sodium lauryl sulfate, or lecithin.

9. The process of claim 1 wherein the redispersibility excipient is a salt, sugar, sugar alcohol, or polysaccharide.

10. The process of claim 1 wherein the redispersibility excipient is a monosaccharide, a disaccharide, an amino acid or a sugar alcohol.

11. The process of claim 10 wherein the sugar alcohol is selected from mannitol, xylitol, sorbitol, and glycerol.

12. The process of claim 11 wherein the sugar alcohol is mannitol.

13. The process of claim 1 wherein the amount of active ingredient in the dried-solids containing slurry is between about 20-80 wt/wt %.

14. The process of claim 13 wherein the amount of active ingredient in the dried-solids containing slurry is between about 35-65 wt/wt %.

15. The process of claim 1, wherein:
the steric stability polymer is selected from one or more of hydroxypropyl cellulose, hydroxypropyl methyl cellulose, polyvinyl pyrrolidone, poly(butyl methacrylate-co-(2-dimethylaminoethyl), and polyethylene glycol;
the electrostatic stability surfactant is selected from one or more of sodium lauryl sulfate, Polysorbate 80, and sorbitan monostearate; and
the redispersibility excipient is selected from one or more of lactose, mannitol, sucrose, and trehalose.

\* \* \* \* \*